US009663437B2

(12) United States Patent
Torrence et al.

(10) Patent No.: US 9,663,437 B2
(45) Date of Patent: *May 30, 2017

(54) PRODUCTION OF ACETIC ACID WITH HIGH CONVERSION RATE

(75) Inventors: G. Paull Torrence, League City, TX (US); Brian W. Hokkanen, Houston, TX (US); Ronald David Shaver, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 1108 days.

This patent is subject to a terminal disclaimer.

(21) Appl. No.: 13/368,880

(22) Filed: Feb. 8, 2012

(65) Prior Publication Data

US 2013/0066107 A1   Mar. 14, 2013

Related U.S. Application Data

(63) Continuation-in-part of application No. 13/231,205, filed on Sep. 13, 2011, now Pat. No. 8,877,963.

(51) Int. Cl.
*C07C 51/12* (2006.01)
*C07C 51/44* (2006.01)

(52) U.S. Cl.
CPC .............. *C07C 51/12* (2013.01); *C07C 51/44* (2013.01)

(58) Field of Classification Search
None
See application file for complete search history.

(56) References Cited

U.S. PATENT DOCUMENTS

| | | |
|---|---|---|
| 3,769,329 A | 10/1973 | Paulik et al. |
| 4,994,608 A | 2/1991 | Torrence et al. |
| 5,001,259 A | 3/1991 | Smith et al. |
| 5,026,908 A | 6/1991 | Smith et al. |
| 5,144,068 A | 9/1992 | Smith et al. |
| 5,334,755 A | 8/1994 | Yoneda et al. |
| 5,380,929 A | 1/1995 | Erpenbach et al. |
| 5,391,821 A | 2/1995 | Koyama et al. |
| 5,599,976 A | 2/1997 | Scates et al. |
| 5,672,744 A | 9/1997 | Kagotani et al. |
| 5,683,492 A | 11/1997 | Hesse et al. |
| 5,696,284 A | 12/1997 | Baker et al. |
| 5,731,252 A | 3/1998 | Warner et al. |
| 5,840,969 A | 11/1998 | Joensen |
| 5,877,347 A | 3/1999 | Ditzel et al. |
| 5,877,348 A | 3/1999 | Ditzel et al. |
| 5,883,295 A | 3/1999 | Sunley et al. |
| 5,883,764 A | 3/1999 | Pinarbasi |
| 5,917,089 A * | 6/1999 | Howard ............... C07C 51/12 560/129 |
| 5,932,764 A | 8/1999 | Morris et al. |
| 5,942,460 A | 8/1999 | Garland et al. |
| 6,140,535 A | 10/2000 | Williams |
| 6,143,930 A | 11/2000 | Singh et al. |
| 6,153,792 A | 11/2000 | Leet et al. |
| 6,232,352 B1 | 5/2001 | Vidalin |
| 6,339,171 B1 | 1/2002 | Singh et al. |
| 6,462,231 B1 | 10/2002 | Yanagawa et al. |
| 6,617,471 B2 | 9/2003 | Zoeller et al. |
| 6,627,770 B1 | 9/2003 | Cheung et al. |
| 6,657,078 B2 | 12/2003 | Scates et al. |
| 6,727,380 B2 | 4/2004 | Ellis et al. |
| 7,005,541 B2 | 2/2006 | Cheung et al. |
| 7,115,772 B2 | 10/2006 | Picard et al. |
| 7,202,382 B2 | 4/2007 | Muskett |
| 7,208,624 B2 | 4/2007 | Scates et al. |
| 7,223,886 B2 | 5/2007 | Scates et al. |
| 7,473,800 B2 | 1/2009 | Hosono et al. |
| 7,678,940 B2 | 3/2010 | Miura et al. |
| 7,683,212 B2 | 3/2010 | Kojima et al. |
| 8,877,963 B2 | 11/2014 | Hokkanen et al. |
| 2003/0199711 A1 | 10/2003 | Broussard et al. |
| 2005/0165251 A1* | 7/2005 | Muskett ................ C07C 51/12 562/519 |

(Continued)

FOREIGN PATENT DOCUMENTS

| | | |
|---|---|---|
| CN | 1537840 | 10/2004 |
| CN | 101439256 | 5/2009 |
| EP | 2 093 209 A1 | 8/2009 |
| JP | 2-104551 A | 4/1990 |
| JP | 8-188547 | 7/1996 |
| JP | 10-245362 A | 9/1998 |
| JP | 2006-182691 A | 7/2006 |
| JP | 2011-512391 A | 4/2011 |
| JP | 2013-540763 A | 11/2013 |
| WO | WO 2007/107724 | 9/2007 |
| WO | WO 2012/050846 A1 | 4/2012 |

OTHER PUBLICATIONS

International Search Report and Written Opinion mailed Feb. 6, 2013 in corresponding International Application No. PCT/US2012/052829.

(Continued)

*Primary Examiner* — Matthew Coughlin
*Assistant Examiner* — Po-Chih Chen
(74) *Attorney, Agent, or Firm* — Kilpatrick Townsend & Stockton LLP

(57) ABSTRACT

A process for producing acetic acid comprising the steps of reacting carbon monoxide and at least one of methanol and a methanol derivative in a first reactor under conditions effective to produce a crude acetic acid product; separating the crude acetic acid product into at least one derivative stream, at least one of the at least one derivative stream comprising residual carbon monoxide; and reacting at least a portion of the residual carbon monoxide with at least one of methanol and a methanol derivative over a metal catalyst in a second reactor to produce additional acetic acid. Preferably the second reactor is a homogeneous reactor and a reactor carbon monoxide partial pressure is less than 1.05 MPa.

22 Claims, 3 Drawing Sheets

(56) References Cited

U.S. PATENT DOCUMENTS

| | | | |
|---|---|---|---|
| 2008/0287706 A1 | 11/2008 | Powell et al. | |
| 2008/0293966 A1 | 11/2008 | Scates et al. | |
| 2009/0107833 A1 | 4/2009 | Warner | |
| 2009/0270650 A1 | 10/2009 | Patt | |
| 2009/0270651 A1 | 10/2009 | Zinobile et al. | |
| 2010/0069514 A1 | 3/2010 | Gracey et al. | |
| 2012/0078011 A1* | 3/2012 | Zinobile | 562/518 |
| 2012/0078012 A1* | 3/2012 | Torrence et al. | 562/519 |
| 2013/0172614 A1* | 7/2013 | Torrence et al. | 562/519 |

OTHER PUBLICATIONS

International Search Report and Written Opinion mailed Jan. 25, 2012 in corresponding International Application No. PCT/US2011/053539.

International Search Report and Written Opinion mailed Jan. 25, 2012 in corresponding International Application No. PCT/US2011/053369.

J. H. Jones (2002), "The Cativa™ Process for the Manufacture of Acetic Acid", Platinum Metals Review, 44(3): 94-105.

Michael Gauβ, et al., Applied Homogeneous Catalysis with Organometallic Compounds: A Comprehensive Handbook in Two Volume, Chapter 2.1, pp. 27-200, (1st ed., 1996).

Noriyuki Yoneda and Yasuo Hosono (2004); "Acetic Acid Process Catalyzed by Ionically Immobilized Rhodium Complex to Solid Resin Support", Journal of Chemical Engineering of Japan, vol. 34, No. 4, 536-545.

International Search Report and Written Opinion mailed on Jan. 25, 2012 in corresponding International Application No. PCT/US11/53539.

International Search Report and Written Opinion mailed on Jan. 25, 2012 in corresponding International Application No. PCT/US2011/053369.

* cited by examiner

PRODUCTION OF ACETIC ACID WITH HIGH CONVERSION RATE

CROSS-REFERENCE TO RELATED APPLICATIONS

This application is a continuation-in-part of and claims priority to U.S. patent application Ser. No. 13/231,205, filed on Sep. 13, 2011, the disclosure of which is hereby incorporated by reference.

FIELD OF THE INVENTION

This invention relates to processes for producing acetic acid from carbon monoxide and, in particular, to improved processes, which react residual carbon monoxide to form additional acetic acid, thus improving the overall conversion of the carbon monoxide feed.

BACKGROUND OF THE INVENTION

A widely used and successful commercial process for synthesizing acetic acid involves the catalyzed carbonylation of methanol with carbon monoxide. The catalysis contains rhodium and/or iridium and a halogen promoter, typically methyl iodide. The reaction is conducted by continuously bubbling carbon monoxide through a liquid reaction medium in which the catalyst is dissolved. The reaction medium also comprises methyl acetate, water, methyl iodide and the catalyst. Conventional commercial processes for carbonylation of methanol include those described in U.S. Pat. Nos. 3,769,329, 5,001,259, 5,026,908, and 5,144,068, the entire contents and disclosures of which are hereby incorporated by reference. Another conventional methanol carbonylation process includes the Cativa™ process, which is discussed in Jones, J. H. (2002), "The Cativa™ Process for the Manufacture of Acetic Acid," Platinum Metals Review, 44 (3): 94-105, the entire content and disclosure of which is hereby incorporated by reference.

During the methanol carbonylation reaction, by-product gases build up in the reactor as the crude acetic acid product is withdrawn into a flasher. The build-up of these gases in the reactor is often controlled by venting an off-gas from the reactor to keep the carbon monoxide partial pressure in the reactor at an acceptable level to maximize catalyst activity and stability. The vented off-gas may comprise carbon monoxide, inert and by-product gases, volatile halogen promoters, acetic acid, water, unreacted methanol, and/or methyl acetate. In most methanol carbonylation processes the off-gas is processed in one or more recovery units to recover volatile halogen promoters, acetic acid, water, unreacted methanol, and/or methyl acetate and return those recovered compounds to the reactor. The gases that pass out of the recovery units may be purged and/or directed to a flasher vessel to enhance catalyst stability. An example of a recovery unit is described in U.S. Pub. Nos. 2008/0293996 and 2009/0270651, the entire contents and disclosure of which are hereby incorporated by reference.

U.S. Pat. No. 5,917,089 discloses that an "off-gas" from the reactor may be fed directly to a second reactor, along with fresh methanol, to produce additional carbonylation product, i.e. acetic acid. The off-gas, as known in the art, however, is not a derivative stream.

A purification section processes the crude acetic acid product from the reactor to remove impurities thus providing a high quality acetic acid product. These impurities, which may be present in trace amounts, affect the quality of acetic acid, especially as the impurities are circulated through the reaction process, which, among other things, can result in the build up over time of these impurities. Conventional purification techniques to remove these impurities include treating the acetic acid product streams with oxidizers such as ozone, reducers such as hydrogen, water, methanol, activated-carbon, amines, and the like. The treatments may or may not be combined with the distillation of the crude acetic acid product. Typically, during the purification, there are several vents, which purge non-condensable gases formed in the reactor. The vented gases may be processed in a recovery unit to recover light boiling point components, such as the halogen promoter, as described in U.S. Pub. No. 2008/0293966, the entire content and disclosure of which is hereby incorporated by reference. The vented gases, which also contain carbon monoxide, that pass through the recovery unit are typically purged or flared. The loss of the carbon monoxide represents a loss of the reactants.

An alternative to the liquid-phase methanol carbonylation process is described in U.S. Pat. No. 6,617,471, the entire contents and disclosures of which are hereby incorporated by reference. U.S. Pat. No. 6,617,471 discloses a vapor-phase carbonylation method for producing esters and carboxylic acids from reactants comprising lower alkyl alcohols, lower alkyl alcohol generating compounds, and mixtures thereof. The method includes contacting the reactants and carbon monoxide in a carbonylation zone of a carbonylation reactor under vapor-phase conditions with a catalyst having a catalytically effective amount of iridium and tin associated with a solid carrier material.

In view of these references, the need exists for improved processes for processing vented gases during the purification and separation of the crude acetic acid product to recover reactants and improve the efficiency of the acetic acid production.

SUMMARY OF THE INVENTION

The present invention is to processes for producing acetic acid. In a first embodiment, the process comprises the step of reacting a first reaction mixture in a first reactor under conditions effective to produce a crude acetic acid product. The first reaction mixture comprises carbon monoxide and at least one of methanol and a methanol derivative. The process further comprises the steps of separating the crude acetic acid product into at least one derivative stream comprising residual carbon monoxide. The process may also comprise the step of reacting a second reaction mixture in a second reactor to produce additional acetic acid. The second reaction mixture comprises 1) at least a portion of the residual carbon monoxide in the at least one derivative stream and 2) at least one of methanol and a methanol derivative. Preferably, the second reactor is a homogeneous reactor and the second reactor operates at a low carbon monoxide partial pressure, e.g., a reactor carbon monoxide partial pressure less than 1.05 MPa.

In another embodiment, the process comprises the step of reacting in a reactor a carbon monoxide feed, e.g., a lower carbon monoxide content feed, and at least one of methanol and a methanol derivative under conditions effective to produce a reaction product and a vent stream. The reaction product comprises a crude acetic acid product and the vent stream comprising less than 60 mol % carbon monoxide. Preferably, the reaction in the reactor is a homogeneous reaction and the reaction is conducted at a carbon monoxide partial pressure less than 1.05 MPa.

BRIEF DESCRIPTION OF DRAWINGS

The invention is described in detail below with reference to the appended drawings, wherein like numerals designate similar parts.

DETAILED DESCRIPTION OF THE INVENTION

Introduction

Figure 1:
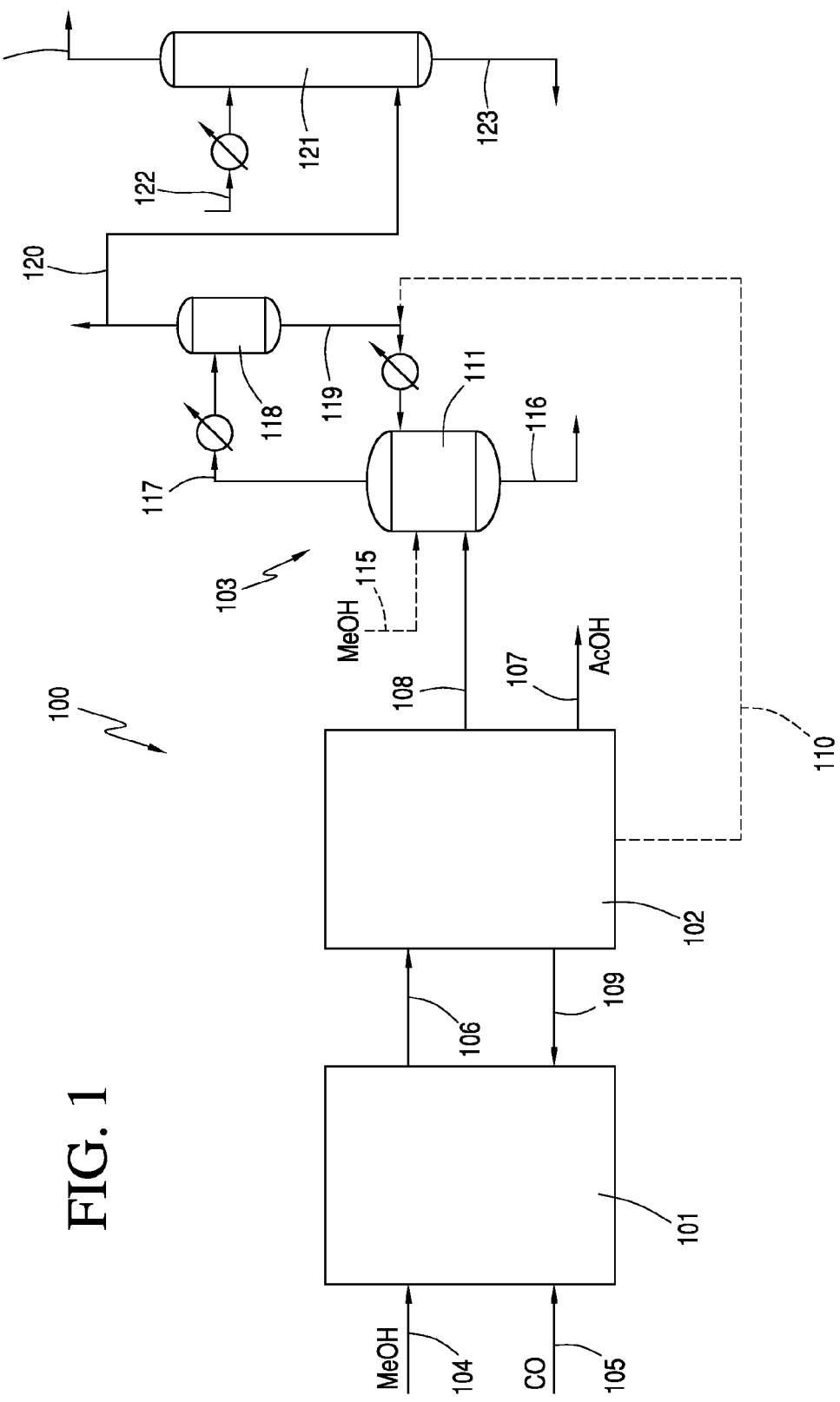
FIG. 1 is a schematic diagram of an exemplary process comprising a homogeneous, high pressure, liquid phase carbonylation secondary reactor for processing a purged derivative stream from an acetic acid purification section in accordance with an embodiment of the present invention.

The present invention generally relates to the production of acetic acid from unreacted, e.g., residual, carbon monoxide that may be present in one or more derivative streams of a crude acetic acid product. The derivative stream(s) are obtained during the purification and separation of the crude acetic acid product. For purposes of the present application, the separation zone refers to the portion of the process that purifies or separates the crude acetic acid product. In a preferred embodiment, the derivative stream(s) are vented gas streams of the separation zone. In one embodiment, the processes of the present invention advantageously increase the overall carbon monoxide efficiency by utilizing the residual carbon monoxide in the derivative streams to form additional acetic acid. In another embodiment, the processes of the present invention advantageously reduce the amount of carbon monoxide that is purged or flared from the purification and separation section.

The present invention, in one embodiment, relates to a process for producing acetic acid. The process comprises the step of reacting a first reaction mixture in a first reactor and under conditions effective to produce a crude acetic acid product. The first reaction mixture may comprise 1) carbon monoxide; and 2) methanol and/or a methanol derivative. The crude acetic acid product comprises, inter alia, acetic acid and residual carbon monoxide. The residual carbon monoxide may be dissolved and/or entrained in the crude acetic acid product. The inventive processes further comprise the steps of separating the crude acetic acid product into at least one derivative stream comprising residual carbon monoxide; and reacting a second reaction mixture in a second reactor and under conditions effective to produce additional acetic acid. The second reaction mixture comprises 1) at least a portion of the residual carbon monoxide in the at least one derivative stream; and 2) methanol and/or a methanol derivative, e.g., methyl acetate, dimethyl ether, methyl formate and/or dimethyl carbonate. Preferably, the second reactor is a homogeneous reactor. In preferred embodiments, a reactor carbon monoxide partial pressure (in the second reactor) is less than 1.05 MPa, e.g., less than 1 MPa, less than 0.9 MPa, less than 0.75 MPa, or less than 0.5 MPa. In terms of ranges, the reactor carbon monoxide partial pressure may range from 0.005 MPa to 1.05 MPa, e.g., from 0.01 MPa to 1 MPa, from 0.1 MPa to 0.9 MPa, from 0.005 MPa to 0.15 MPa, or from 0.05 to 0.15. In one embodiment, the reactor carbon monoxide partial pressure is the carbon monoxide partial pressure in a headspace of the second reactor. Unlike the primary reactor of the invention and unlike conventional carbonylation reactors, the inventive secondary carbonylation reactor operates with a low reactor carbon monoxide partial pressure. The low reactor carbon monoxide partial pressure of the pressure invention is significantly different from conventional reactors that may carbonylate conventional off-gas streams. These conventional reactors utilize feed streams having much higher carbon monoxide partial pressures.

It has now been discovered, surprisingly and unexpectedly, that suitable carbon monoxide conversions, acetic acid selectivities, and overall product yields can be achieved even when the second reactor is operated at the low reactor carbon monoxide partial pressures discussed above. In one embodiment the carbon monoxide conversion in the second reactor is at least 30%, e.g., at least 60%, at least 90%, or at least 95%. In one embodiment, the selectivity to carbonylated product(s), e.g., acetic acid, methyl acetate, and mixtures thereof, is at least 20%, e.g., at least 60%, or at least 90%. In one embodiment, the acetic acid selectivity in the second reactor is at least 20%, e.g., at least 60% or at least 90%. These conversions and selectivities are achieved by employing a homogeneous reactor as the second reactor. Conventional reaction schemes, e.g., heterogeneous reactors, typically require significantly higher reactor carbon monoxide partial pressures to achieve similar carbon monoxide conversions, acetic acid selectivities, and product yields. Without being bound by theory, it is believed that the use of a homogeneous reactor allows for reduction or elimination of a reactor vent stream. The reactor vent stream vents from the reactor by-product gasses, which typically contain amounts of carbon monoxide. These vent streams are required in conventional heterogeneous reaction schemes. By reducing the size of the reactor vent stream (or eliminating the reactor vent stream entirely), less carbon monoxide is vented from the process, e.g., wasted, and conversions are improved.

In the processes of the present invention, less carbon monoxide is wasted through venting and the overall carbon monoxide conversion is advantageously improved. In one embodiment, the overall carbon monoxide conversion relates to the conversion of the initial carbon monoxide feed stream in a first reaction and the conversion of residual carbon monoxide in a second reaction. Overall carbon monoxide conversions, are preferably greater than 90%, e.g., greater than 95%, greater than 99%, or greater than 99.5%.

As another benefit, the low reactor carbon monoxide partial pressures of the present invention allow the second reactor to be operated at lower overall pressure without risk of significant catalyst precipitation. In some embodiments, even if some catalyst may precipitate, the precipitated catalyst may be collected and recycled, e.g., used in the primary reactor. Because this catalyst can be more easily collected and recycled, the need for a flasher downstream of the second reactor is reduced or eliminated.

In a preferred embodiment, catalyst that has precipitated from the reaction mixture of the secondary reactor may be recovered and/or recycled to the primary reactor. In one embodiment, the process further comprises the step of separating the crude acetic acid product to form a catalyst recycle stream. As such, the catalyst that is present in the crude product may be separated, e.g., via a flasher or a light ends column, may be removed from the crude stream. Preferably, at least a portion of the catalyst recycle stream may be directed to the secondary reactor where it may be used in the secondary carbonylation reaction. In one embodiment, a slip stream is taken from a light ends column and/or from a flasher and directed to the secondary reactor.

In another embodiment, the invention relates to a process for producing acetic acid comprising the step of contacting with at least one of methanol and a methanol derivative a carbon monoxide feed stream, e.g., a low carbon monoxide content feed stream, comprising a low concentration of carbon monoxide (as compared to conventional carbon monoxide feed streams), e.g., from 10 mol % to 95 mol %, from 25 mol % to 75 mol % or from 40 mol % to 60 mol % carbon monoxide. Preferably, the low carbon monoxide content feed stream comprises from 60 mol % to about 70 mol % carbon monoxide. In terms of partial pressures, the low carbon monoxide content feed streams optionally have a carbon monoxide partial pressure of from 10% to 95% of the total pressure of the derivative stream(s), e.g., from 25% to 75% or from 40% to 60%. In terms of limits, the low carbon monoxide feed stream preferably comprises less than 95 mol % carbon monoxide, e.g., less than 80 mol %, less than 70 mol %, less than 50 mol %, or less than 40 mol %. In other embodiments, the low carbon monoxide feed stream has a carbon monoxide partial pressure less than 95% of the total pressure of the low carbon monoxide feed stream, e.g., less than 80%, less than 70%, less than 50%, or less than 40%. Again, for carbon monoxide to be reacted with methanol to form acetic acid, some amount of carbon monoxide should be present in the carbon monoxide feed stream. For example, the carbon monoxide feed stream may comprise residual carbon monoxide in an amount greater than 0.1 mol %, greater than 0.5 mol % or greater than 1 mol %; or the carbon monoxide feed stream may have a carbon monoxide partial pressure greater than 0.1% of the total pressure of the low carbon monoxide feed stream, e.g., greater than 0.5% or greater than 1%. The carbon monoxide feed stream may further comprise, for example, methanol and/or a methanol derivative, e.g., methyl acetate, dimethyl ether, and/or methyl formate, which is used to produce an acetic acid composition. In one embodiment, the methanol derivative may be dimethyl carbonate. The inventive process reacts low carbon monoxide feed streams, optionally obtained from vented gases, and thus avoids the waste thereof. Preferably, the contacting step is performed in a homogeneous reactor, as discussed above.

Also, an additional embodiment relates to a process for producing acetic acid comprising the step of contacting a carbon monoxide feed and at least one of methanol and a methanol derivative under conditions effective to produce a reaction product comprising a crude acetic acid product and a vent stream. The vent stream comprises low amounts of carbon monoxide, e.g., less than 60 mol %, e.g., less than 50 mol %, less than 25 mol %; less than 10 mol %; less than 5 mol %; or less than 1 mol %. In terms of ranges, the vent stream may comprise from 0.1 mol % to 60 mol % carbon monoxide, e.g., from 1 mol % to 50 mol %, or from 5 mol % to 25 mol %. In another embodiment, the vent stream has a carbon monoxide partial pressure less than 60% of the total pressure of the vent stream, e.g., less than 50%, less than 25%, less than 10%, less than 5%, or less than 1%. The reaction is conducted using a homogeneous reactor and at a carbon monoxide partial pressure less than 1.05 MPa.

Primary Carbonylation

The features of the present invention may be applied to any suitable carbon monoxide/methanol carbonylation process. The process conditions for the primary carbonylation reaction in the first reactor (and those of the secondary carbonylation in the second reactor) may vary widely. As one example, methanol and/or methanol derivative(s) may be reacted with carbon monoxide to form the crude acetic acid product, which comprises a major portion of acetic acid.

Preferably, the first reactor is a continuous stirred tank reactor ("CSTR"). When using a CSTR, the catalyst is dissolved in the reaction solvent and liquid methanol and carbon monoxide gas are injected from the bottom as reaction raw materials and made to react with one another. When a CSTR is utilized, the CSTR may be adapted to agitate the reaction solution by an agitation device such as an impeller, although the agitation device is not required. Alternatively, a bubble column reactor may be utilized as the first reactor to perform the carbonylation. When a bubble column reactor is utilized, a cylindrical reactor is filled with a reaction solvent and a solid catalyst. Liquid methanol is supplied from the bottom as reaction raw material while carbon monoxide gas is injected upward from the bottom as jet stream. The injected carbon monoxide gas forms bubbles as it rises in the liquid contained in the cylindrical reactor and particles of the catalyst are also driven to move upward in the cylindrical reactor by the gas lift effect and dispersed into the liquid. As one example, the carbon monoxide may be injected into the liquid contained in a cylindrical reactor as jet stream by way of a nozzle arranged at the bottom of the cylindrical reactor for the purpose of mobilizing particles of the solid catalyst in the reactor, as disclosed in Japanese Patent Application Laid-Open No. 6-340242, which is hereby incorporated by reference in its entirety. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference in its entirety. In some embodiments, the first reactor is either a CSTR or bubble-column type vessel, with or without an agitator, and the reaction mixture is maintained therein, preferably automatically, at a predetermined level. This predetermined level may remain substantially constant during normal operation. Generally speaking, methanol, carbon monoxide, and sufficient water may be continuously introduced in to the first reactor as needed to maintain at least a finite concentration of water in the reaction medium.

In one embodiment, the reaction in the first reactor is conducted using a homogeneous reaction mixture, e.g., a homogeneous catalytic reaction system, comprising a reaction solvent, methanol and/or reactive derivatives thereof, a Group VIII catalyst, at least a finite concentration of water, and optionally an iodide salt. In another embodiment, the reaction in the first reactor is conducted using a heterogeneous reaction mixture, e.g., a heterogeneous catalytic reaction system. If a heterogeneous reaction mixture is employed, in some embodiments, the catalyst recycle stream is not utilized to supply catalyst to the secondary reactor.

Suitable Group VIII catalysts include rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael Gauβ, et al., Applied Homogeneous Catalysis with Organometallic Compounds: A Comprehensive Handbook in Two Volume, Chapter 2.1, p. 27-200, (1st ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, the catalyst co-promoter is lithium iodide, lithium acetate, or mixtures thereof. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, the entireties of which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)2I]_2$, $[Ir(CO)2Cl]_2$, $[Ir(CO)2Br]_2$, $[Ir(CO)2I_2]$-$H^+$, $[Ir(CO)2Br_2]$-$H^+$, $[Ir(CO)2I_4]$-$H^+$, $[Ir(CH_3)I_3(CO_2)]$-$H^+$, $Ir_4(CO)_{12}$, $IrCl_3 \cdot 3H_2O$, $IrBr_3 \cdot 3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

An alkyl halide co-catalyst/promoter is generally used in combination with the Group VIII metal catalyst component. Methyl iodide is preferred as the alkyl halide promoter. Preferably, the concentration of alkyl halide in the liquid reaction composition is in the range of 1 to 50% by weight, preferably 5 to 20%.

The halogen promoter may be combined with a salt stabilizer/co-promoter compound, which may include salts of a metal of Group IA or Group IIA, a quaternary ammonium, phosphonium salt or mixtures thereof. Particularly preferred are iodide or acetate salts, e.g., lithium iodide or lithium acetate.

Other promoters and co-promoters may be used as part of the catalytic system of the present invention as described in U.S. Pat. No. 5,877,348, the entirety of which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, the entirety of which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 ppm.

In one embodiment, the temperature of the carbonylation reaction in the first reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa.

In one embodiment, the first reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

The methanol feed stream fed to the first reactor comprises methanol and/or reactive derivatives thereof. Suitable reactive derivatives of methanol include methyl acetate, dimethyl ether, and methyl formate. In one embodiment, a mixture of methanol and reactive derivatives thereof may be used as reactants in the process of the present invention. Preferably, methanol and/or methyl acetate are used as reactants. At least some of the methanol and/or reactive derivative thereof will be converted to, and hence present as, methyl acetate in the liquid reaction composition by reaction with acetic acid product or solvent. The concentration in the liquid reaction mixture of methyl acetate is suitably in the range of from 0.5 wt. % to 70 wt. %, e.g., from 0.5 wt. % to 50 wt. %, from 1 wt. % to 35 wt. %, or from 1 wt. % to 20 wt. %.

The carbon monoxide feed stream fed to the first reactor may be essentially pure or may contain small amounts of inert impurities such as carbon dioxide, methane, hydrogen, nitrogen, noble gases, water and C1 to C4 paraffinic hydrocarbons. The carbon monoxide feed stream preferably comprises a high content of carbon monoxide, e.g., at least 95 mol %, at least 98 mol %, or at least 99 mol %. The carbon monoxide feed stream preferably has a higher carbon monoxide content relative to the derivative streams fed to secondary reaction zone.

The carbon monoxide feed stream may also be characterized in terms of partial pressure. The carbon monoxide feed stream may have a carbon monoxide partial pressure of at least 95% of the total pressure of carbon monoxide feed stream 105, e.g., at least 98% or at least 99%. In one embodiment, the partial pressure of carbon monoxide in the carbon monoxide feed ranges from 0.1 MPa to 7 MPa, e.g., from 0.1 MPa to 3.5 MPa, or from 0.1 MPa to 1.5 MPa. Hydrogen may be generated in the carbon monoxide feed stream by the water gas shift reaction. Preferably, the partial pressure of hydrogen is maintained at a low level, for example, less than 0.1 MPa or less than 0.05 MPa, as the presence of hydrogen may result in the formation of various hydrogenation products.

The raw materials used in connection with the process of this invention may be derived from any suitable source including natural gas, petroleum, coal, biomass, and so forth.

As petroleum and natural gas prices fluctuate becoming either more or less expensive, methods for producing acetic acid intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. Accordingly, in some embodiments, some or all of the raw materials for the above-described carbonylation may be derived partially or entirely from syngas. For example, both the methanol and carbon monoxide may be derived from syngas. The syngas may be formed by partial oxidation reforming or steam reforming, and the carbon monoxide may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

Also, U.S. Pat. No. RE 35,377, incorporated herein by reference, discloses a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid.

The acetic acid, in turn, may be hydrogenated to form ethanol and/or ethanol derivatives. Processes for hydrogenating acetic acid to form ethanol are described, for example, in U.S. Pat. Nos. 7,608,744; 7,863,489; US Publication Nos. US2010/0197985; US2011/0190547; US2011/0190548; US2011/0275862; US2011/0282110; and in U.S. patent application Ser. Nos. 13/197,743; 13/197,738; 13/299,816, each of which is incorporated herein by reference in its entirety.

Returning to the carbonylation reaction, water may be formed in situ in the liquid reaction composition, for example, by the esterification reaction between methanol reactant and acetic acid product. Water may be introduced to the carbonylation reactor together with or separately from other components of the liquid reaction composition. Water may be separated from other components of reaction composition withdrawn from the reactor and may be recycled in controlled amounts to maintain the required concentration of water in the liquid reaction composition. Preferably, the concentration of water maintained in the liquid reaction composition is in the range of from 0.1 wt. % to 16 wt. %, e.g., from 1 wt. % to 14 wt. %, or from 1 wt. % to 10 wt. %.

In one embodiment, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The concentration of iodide ion maintained in the reaction medium of the preferred carbonylation reaction system is believed to be quite high as compared with what little prior art there is dealing with the use of halide salts in reaction systems of this sort. The absolute concentration of iodide ion content is not a limitation on the usefulness of the present invention.

As noted above, the carbonylation reaction of methanol to acetic acid product may be carried out by contacting the methanol feed with gaseous carbon monoxide bubbled through an acetic acid solvent reaction medium containing the catalyst e.g., rhodium or iridium, methyl iodide promoter, methyl acetate, and/or additional soluble iodide salt, at conditions of temperature and pressure suitable to form the carbonylation product. Without being bound by theory, it is generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt % to 30 wt. %, e.g., from 1 wt. % to 25 wt. %, or from 2 wt. % to 20 wt. %; and the lithium iodide may be present in amounts ranging from 5 wt. % to 20 wt %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

The primary carbonylation reaction yields a crude acetic acid product, which comprises a major portion of acetic acid. For example, the crude acetic acid product may comprise at least 50 mol % acetic acid, e.g., at least 60 mol %, at least 75 mol %, at least 90 mol %, at least 95 mol %, or at least 98 mol %. In terms of upper limits, the crude acetic acid product may comprise less than 99.9 mol % acetic acid, e.g., less than 99 mol % or less than 95 mol %. In terms of ranges, the crude acetic acid product optionally comprises from 50 mol % to 99.9 mol % acetic acid, e.g., from 60 mol % to 99 mol %, or from 75 mol % to 95 mol %.

In other embodiments, the crude acetic acid product may have an acetic acid partial pressure of at least 50% of the total pressure of the crude acetic acid product, e.g., at least 75%, at least 90%, at least 95%, or at least 98%. In terms of upper limits, the crude acetic acid product may have an acetic acid partial pressure of less than 99.9% of the total pressure of the crude acetic acid product, e.g., less than 99% or less than 95%. In terms of ranges, the acetic acid partial pressure may range from 50% to 99.9% of the total pressure of the crude acetic acid product, e.g., from 60% to 99% or from 75% to 95%. Optionally, the crude acetic acid product further comprises methyl iodide (liquid and/or vapor), methyl acetate, propionic acid, water, residual catalyst, and acetaldehyde. In one embodiment, the crude acetic acid product may comprise acetic acid, residual catalyst, dissolved and/or entrained carbon monoxide, methyl iodide, methyl acetate, water, permanganate reducing compounds ("PRCs"), and/or other dissolved gases such as carbon dioxide, hydrogen, and methane.

The crude acetic acid product may further comprise residual carbon monoxide. In one embodiment, the crude acetic acid product comprises residual carbon monoxide in an amount less than 20 mol %, e.g., less than 10 mol %, less than 5 mol %, or less than 3 mol %. Of course, for residual carbon monoxide to be reacted with methanol and/or a methanol derivative to form additional acetic acid, some amount of carbon monoxide should be present. For example, the crude acetic acid product may comprise residual carbon monoxide in an amount greater than 0.1 mol %, greater than 0.5 mol % or greater than 1 mol %. In terms of ranges, the crude acetic acid product may comprise from 0.1 mol % to 20 mol % carbon monoxide, e.g., residual carbon monoxide, e.g., from 0.5 mol % to 10 mol % or from 1 mol % to 5 mol %.

In another embodiment, a flashed vapor phase crude acetic acid product has a carbon monoxide partial pressure that is less than 20% of the total pressure of the flashed crude acetic acid product, e.g., less than 10%, less than 5%, or less than 3%. In terms of partial pressures, the flashed crude acetic acid product may have a carbon monoxide partial pressure of at least 0.1% of the total pressure of the flashed crude acetic acid product, e.g., at least 0.5% or at least 1%. The crude acetic acid product optionally has a carbon monoxide partial pressure of from 0.1% to 20% of the total pressure of the crude acetic acid product, e.g., from 0.5% to 10% or from 1% to 5%.

In another embodiment, the flashed crude acetic acid product is at a total pressure of 0.3 MPa and has a carbon monoxide partial pressure of less than 0.06 MPa, e.g., less than 0.03 MPa; less than 0.015 MPa; or less than 0.009 MPa. In one embodiment, the flashed crude acetic acid product is at 0.3 MPa total pressure and the carbon monoxide partial pressure may be of at least 0.0003 MPa, e.g., at least 0.0015 MPa or at least 0.003 MPa.

Separation

As noted above, the inventive processes comprise the step of separating the crude acetic acid product into one or more derivative streams. At least one of the derivative streams, e.g., at least two or at least three, comprises at least a portion of the residual carbon monoxide. Preferably, the at least one of the derivative streams is a vapor. Residual carbon monoxide, e.g., unreacted carbon monoxide, includes carbon monoxide that has not reacted in the carbonylation reaction and, as such, remains in the crude acetic acid product. In one embodiment, the residual carbon monoxide in the derivative stream(s) is entrained in the respective stream. Without being bound by theory, it is believed that the entrainment of the carbon monoxide is due to the carbon monoxide being conveyed through the liquid reaction mixture. In contrast, a typical off-gas stream is simply a stream that is removed from the vapor built up in the reactor. Thus, the carbon monoxide in conventional off-gas streams is not entrained in the stream.

In one embodiment, the derivative stream(s) comprise less carbon monoxide than the carbon monoxide fed to the primary reactor, e.g., the first reactor. In one embodiment, the derivative stream(s) comprise less than 95 mol % carbon monoxide, e.g., less than 80 mol %, less than 75 mol %, less than 60 mol %, less than 50 mol %, or less than 40 mol %. In another embodiment, the vapor phase derivative stream(s) have a carbon monoxide partial pressure of less than 95% of the total pressure of the vapor phase derivative stream(s), e.g., less than 75%, less than 60%, less than 50%, or less than 40%. In terms of ranges, the derivative stream(s) optionally comprise from 10 mol % to 95 mol % residual carbon monoxide, e.g., from 25 mol % to 75 mol %, or from 40 mol % to 60 mol %. Preferably, the derivative stream(s) comprise from 60 mol % to 70 mol % carbon monoxide. In one embodiment, the concentration of carbon monoxide in the derivative stream(s) may be at least 5% lower than the concentration of the carbon monoxide fed to the reaction zone 101, e.g., at least 10% lower, at least 25% lower, or at least 50% lower. In other embodiments, the carbon monoxide concentration of derivative stream 108 (either in mol % or carbon monoxide partial pressure) may be at least 5% lower than the concentration in a conventional off-gas stream, e.g., at least 10% lower, at least 25% lower, or at least 50% lower. In one embodiment, because of the relatively low amount of carbon monoxide in the feed, the molar ratio of other reactants, e.g., methanol and/or methanol derivatives, to carbon monoxide in the second reactor is greater than 0.02:1, e.g., greater than 0.1:1, greater than 0.25:1 or greater than 0.5:1. In terms of partial pressures, the derivative stream(s) optionally have a carbon monoxide partial pressure of from 10% to 95% of the total pressure of the derivative stream(s), e.g., from 25% to 75% or from 40% to 60%. In preferred embodiments, at least a portion of the residual carbon monoxide in the derivative stream(s) is reacted in the second reactor to form additional acetic acid.

In one embodiment, the inventive process further comprises the step of compressing the derivative stream(s) to form a compressed derivative stream(s). Any suitable compression units may be employed to compress the derivative stream(s). In preferred embodiments, the compressed derivative stream(s) have a feed carbon monoxide partial pressure of at least 0.03 MPa, e.g., at least 0.1 MPa, at least 0.5 MPa, or at least 1 MPa. In terms of ranges, the compressed derivative stream(s) may have a feed carbon monoxide partial pressure ranging from 0.03 MPa to 1.75 MPa, e.g., from 0.1 MPa to 1.5 MPa or from 0.1 MPa to 0.5 MPa. The feed carbon monoxide partial pressure is different from the reactor carbon monoxide partial pressure, e.g., the carbon monoxide partial pressure of the vent gas from the headspace of the secondary reactor. In preferred embodiments, at least a portion of the residual carbon monoxide in the compressed derivative stream(s) is reacted in the second reactor to form additional acetic acid. Some exemplary separation schemes are discussed below in detail.

Secondary Carbonylation

As discussed above, the inventive process comprises the step of reacting, in a second reactor, a second reaction mixture to produce additional acetic acid. The second reaction mixture comprises at least a portion of the residual carbon monoxide from the derivative stream(s) and methanol and/or a methanol derivative. The reactor, preferably, is a homogeneous reactor and the secondary (supplemental) carbonylation that takes place in the second reactor may be a homogeneous reaction, e.g., a homogeneous liquid phase reaction. In one embodiment the second reaction mixture is a homogeneous liquid phase reaction mixture. In one embodiment, the reaction is conducted over a homogeneous catalyst, e.g., a liquid phase catalyst. In a preferred embodiment, the methanol and/or methanol derivative and the metal catalyst are liquids and/or are soluble in the reaction medium. By conducting the second carbonylation homogeneously, e.g., in a homogeneous reactor, suitable carbon monoxide conversions, acetic acid selectivities, and overall product yields can be achieved while using a low reactor carbon monoxide partial pressure.

In one embodiment, the first reaction mixture comprises a first amount of rhodium as a catalyst and the second reaction mixture comprises a second amount of rhodium as a catalyst. Preferably, the first amount of rhodium is less than the second amount of rhodium, e.g., at least 10% less than, at least 25% less than, or at least 50% less than. In one embodiment, the first reaction mixture comprises from 300 wppm to 5000 wppm rhodium, e.g., from 900 wppm to 1500 wppm or from 1100 wppm to 1300 wppm. In terms of lower limits, the first reaction mixture comprises at least 300 wppm, e.g., at least 700 wppm, at least 900 wppm or at least 1100 wppm. In terms of upper limits, the first reaction mixture comprises less than 1700 wppm rhodium, e.g., less than 1500 wppm or less than 1300 wppm. In one embodiment, the second reaction mixture comprises from 500 wppm to 6000 wppm rhodium, e.g., from 1500 wppm to 3500 wppm or from 2000 wppm to 3000 wppm. In terms of lower limits, the second reaction mixture comprises at least 500 wppm rhodium, e.g., at least 1000 wppm, at least 1500 wppm or at least 2000 wppm. In terms of upper limits, the second reaction mixture comprises less than 4000 wppm rhodium, e.g., less than 3500 wppm or less than 3000 wppm.

In one embodiment, the pressure in the second reactor is less than the pressure in the first reactor, e.g., at least 10% less, at least 25% less, or at least 50% less. Beneficially, by employing a homogeneous reactor in accordance with the present invention, the need to compress the derivative stream(s) is significantly reduced, which results in increases in overall process efficiency. In one embodiment, the pressure in the second reactor ranges from 0.1 MPa to 10 MPa, e.g., from 1 MPa to 5 MPa or from 2 MPa to 3 MPa. In another embodiment, the temperature in the second reactor ranges from 100° C. to 300° C., e.g., 150° C. to 300° C. or 175° C. to 250° C. In one embodiment, the reaction temperature in the second reactor is similar to the reaction temperature in the first reactor. In other embodiments, however, these two temperatures differ from one another.

Also, the reaction in the second reactor (and optionally that in the first reactor, as well) may be conducted in a counter-current or co-current manner. Although the catalyst for the reaction in the second reactor may be the same as the catalyst in the first reactor, it is preferred that the catalyst in the second reactor is different from the catalyst in the first reactor. Preferably, the catalyst in the second reactor is tailored to account for a carbon monoxide stream that comprises lower amounts of carbon monoxide. Preferably, the catalyst in the second reactor is a rhodium diiodide dicarbonyl anion that is ionically bound to a suitable resin, e.g., polyvinylpyridine or carbon.

The second reactor generally may be any homogeneous reactor suitable for carbonylation of methanol with a relatively low carbon monoxide feed stream. Preferably, the second reactor is a continuous stirred tank reactor ("CSTR"). In one embodiment, a bubble column reactor may be utilized as the second reactor to perform the carbonylation. When these reactors are employed as the secondary reactor, the parameters of these reactors are similar to the parameters discussed above with regard to the first reactor.

In one embodiment, the second reactor comprises a catalyst section and a head space. In a preferred embodiment, the reactor carbon monoxide partial pressure is measured in the head space of the second reactor.

An exemplary carbonylation reaction/separation system is shown in FIG. 1. Carbonylation system 100 comprises carbonylation reaction zone 101, separation zone 102, and secondary reaction zone 103. Other exemplary carbonylation systems, including reaction zone and separation zones, that may be used with embodiments of the present invention include those described in U.S. Pat. Nos. 7,223,886, 7,005,541, 6,657,078, 6,339,171, 5,731,252, 5,144,068, 5,026,908, 5,001,259, 4,994,608, and U.S. Pub. No. 2008/0287706, 2008/0293966, 2009/0107833, 2009/0270651, the entire contents and disclosures of which are hereby incorporated by reference. Exemplary reaction zone 101 and separation zone 102 are shown in the detailed schematic diagrams discussed below with respect to FIGS. 2a and 2b.

Figure 2A:
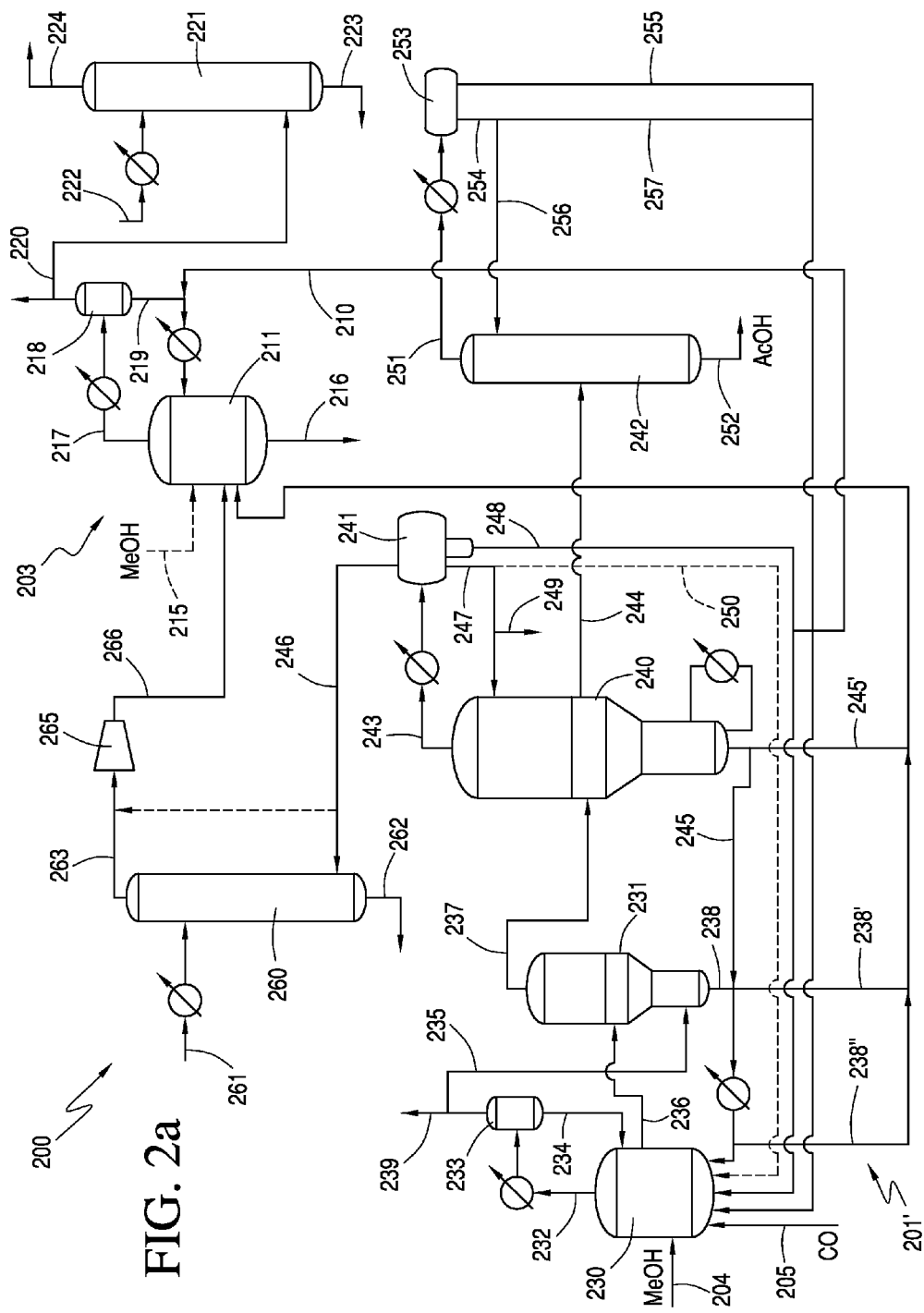
FIG. 2a is a detailed schematic diagram of an exemplary acetic acid production process, which includes reaction and separation, and comprises a homogeneous, high pressure, liquid phase carbonylation secondary reactor in accordance with an embodiment of the present invention.
Figure 2B:
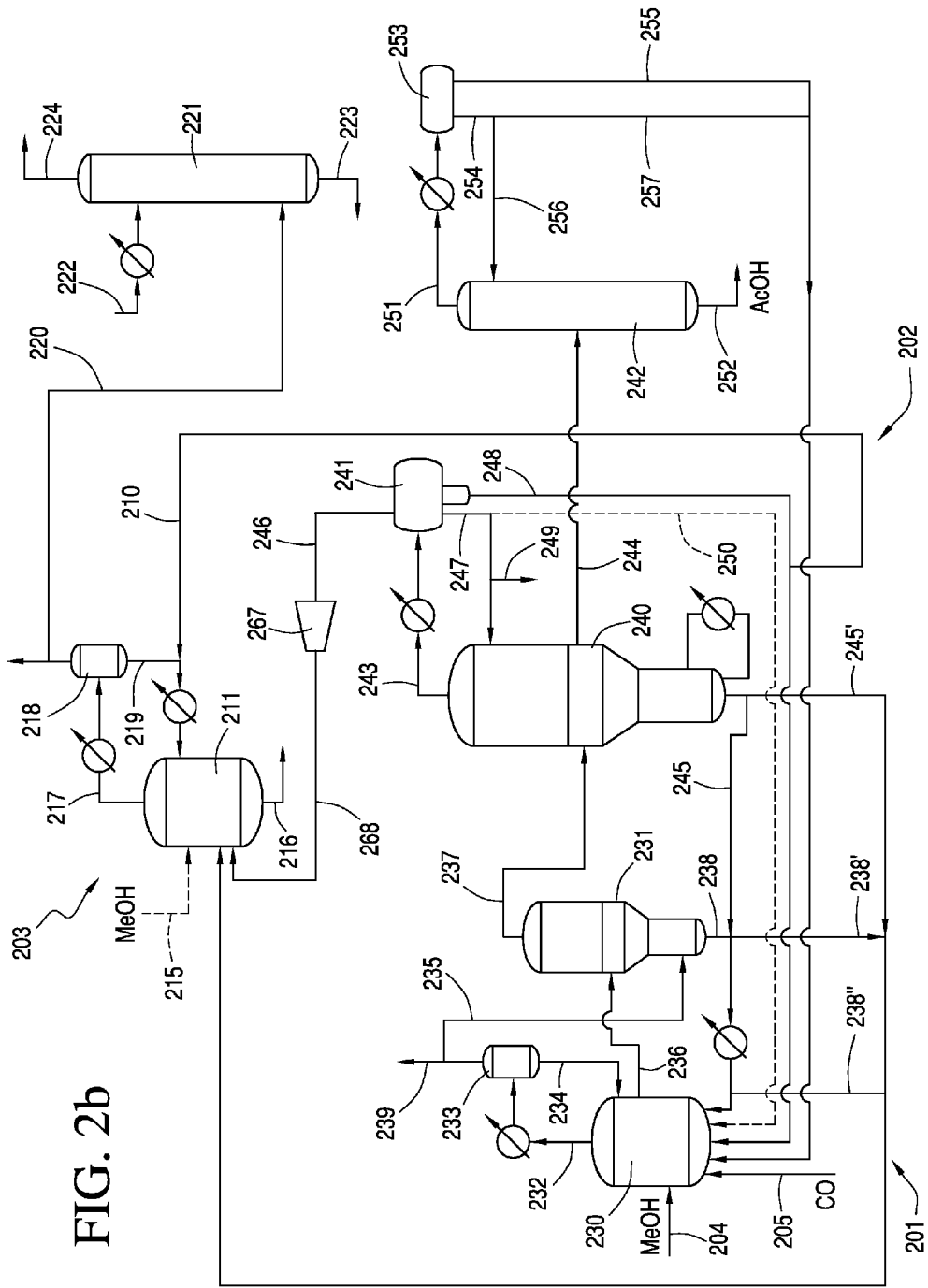
FIG. 2b is a detailed schematic diagram of an exemplary acetic acid production process, which includes reaction and separation, and comprises a homogeneous, high pressure, liquid phase carbonylation secondary reactor in accordance with an embodiment of the present invention.

As shown in FIG. 1, methanol feed stream 104 and carbon monoxide feed stream 105 are fed, preferably continuously fed, to reaction zone 101 to produce crude acetic acid product stream 106. Crude acetic acid product stream 106 may be fed to separation zone 102, which produces purified acetic acid product stream 107 and derivative streams 108, 109, and optional derivative stream 110. Derivative stream 108 may be fed to secondary reaction zone 103. Although derivative stream 108 is shown as a single stream, multiple derivative streams may be yielded by separation zone 102. Derivative stream 109, which may comprise recycled compounds, may be fed, e.g., recycled, to reaction zone 101. In optional embodiments, optional derivative stream 110 may also be fed to secondary reaction zone 103. In one embodiment, the derivative stream(s) are streams that are derived from the crude acetic acid product. For example, the derivative stream(s) may be streams that result from the separation of the crude acetic acid product. As another example, the derivative streams may be stream(s) yielded by a flasher, as shown in FIGS. 2a and 2b. In one embodiment, the derivative stream(s) do not include conventional off-gas streams. Conventional off-gas streams are merely streams of byproduct gases that build up in the reactor as the crude acetic acid product is withdrawn, e.g., withdrawn into a flasher. These off-gas streams essentially comprise reaction by-products, and do not result from the separation of the crude acetic acid product. Thus, conventional off-gas streams are not considered to be derivative streams.

Because the present invention provides for more efficient utilization of residual carbon monoxide, the inventive processes and systems may allow larger quantities of off-gas to be withdrawn from the reactor and/or the flasher. These larger quantities may beneficially be used to supplement other streams in the system, e.g., recycle streams or pump-around streams. In conventional systems, increased off-gas withdrawal would result in increased waste of carbon monoxide.

Derivative stream 108 may be in the liquid-phase or vapor-phase and preferably comprises dissolved and/or entrained carbon monoxide and optionally methanol and/or its reactive derivatives, preferably methyl acetate. In preferred embodiments, derivative stream 108 is in the vapor-phase. In FIG. 1, derivative stream 108 is fed to secondary reactor 111, which preferably is a high pressure liquid phase carbonylation secondary reactor.

In preferred embodiments, the reactants, e.g., methanol and/or methanol derivatives, reacted in second reactor 111 may be present in derivative stream 108. In one embodiment, derivative stream 108 comprises methanol and/or methanol derivative in an amount ranging from 0.1 mol % to 40 mol %, e.g., from 0.5 mol % to 20 mol % or from 1 mol % to 10 mol % other embodiments, derivative stream 108 is in the vapor phase and has a methanol and/or methanol derivative partial pressure of from 0.1% to 40% of the total pressure of derivative stream 108, e.g., from 0.5% to 20% or from 1% to 10% In preferred embodiments the methanol and/or methanol derivative reactant fed to second reactor 111 is methyl acetate. In optional embodiments, fresh methanol and/or methanol derivatives may be fed to second reactor 111 via line 115. In other optional embodiments, methanol and/or methanol derivatives contained in the optional derivative stream 110 from separation zone 102 may be fed to second reactor 111. In other embodiments, derivative stream 108 comprises acetaldehyde. In these embodiments, second reactor 111 may react the acetaldehyde in derivative stream 108 to form other materials. For example, the acetaldehyde may be reacted to form ethanol, which may then be converted to propionic acid, which is easily removed from the product stream. By converting the acetaldehyde in derivative stream 108, acetaldehyde is advantageously removed from derivative stream 108. This reaction of acetaldehyde lowers the amount of acetaldehyde in the product stream and lessens the need for subsequent acetaldehyde removal units, e.g., PRS units.

In FIG. 1, secondary reactor 111 preferably is a high pressure liquid phase carbonylation secondary reactor. The supplemental carbonylation reaction in the secondary reactor 111 is conducted over a liquid-phase homogeneous catalyst. In one embodiment, the liquid-phase homogeneous catalyst comprises metal dissolved in a solution, e.g., rhodium and/or iridium dissolved in acetic acid. Second reactor 111 is preferably operated at lower pressure than that of the primary reactor. In one embodiment, secondary reactor 111 is operated at a temperature similar to that of the primary reactor. In other embodiment, secondary reactor 111 is operated at a temperature that is higher, e.g., at least 5% higher or at least 10% higher, than the temperature of the primary reactor.

Derivative stream 108 is preferably fed to secondary reactor 111 as a liquid or as a condensed vapor stream, optionally with fresh reactants (via line 115), to produce secondary crude product stream 116 comprising acetic acid and overhead stream 117. In one embodiment, the methanol and/or methanol derivative is provided to the second reactor by a supplemental feed stream or by a different derivative stream. Overhead stream 117 comprises methyl iodide, residual carbon monoxide (if any), vaporized methanol, vaporized methyl acetate, and other non-condensable gases such as methane. Overhead stream 117 is condensed and fed to knock-out pot 118 to remove liquid stream 119 and vapor stream 120. Liquid stream 119, along with optional derivative stream 110, is fed to second reactor 111.

Secondary crude product stream 116 may be processed further and fed to the separation zone 102 or may be combined with the purified acetic acid product 107. In some embodiments, secondary crude product stream 116 may be recovered independently of purified acetic acid product 107. Preferably, the secondary crude product stream 116 is enriched in acetic acid relative to derivative stream 108. In one embodiment, secondary crude product stream 116 comprises from 30 mol % to 95 mol % acetic acid, e.g., from 50 mol % to 75 mol % or from 45 mol % to 70 mol %. In terms of limits, secondary crude product stream 116 comprises at least 25 mol % acetic acid, e.g., at least 50 mol %, at least 40 mol % or at least 60 mol %. In terms of partial pressures, secondary crude product stream 116 (when in the vapor phase) may have an acetic acid partial pressure of from 30% to 95% of the total pressure of secondary crude product stream 116, e.g., from 50% to 75% or from 45% to 70%. In one embodiment, secondary crude product stream 116 may further comprise low amounts of carbon monoxide, e.g., less than 40 mol % carbon monoxide, e.g., less than 25 mol %, less than 10 mol %, less than 5 mol %, or less than 3 mol %. In other embodiments, secondary crude product stream 116 may further comprise methanol and/or methanol derivatives in an amount less than 50 mol %, e.g., less than 40 mol %, less than 25 mol % or less than 15 mol %. In terms of ranges secondary crude product stream 116 may comprise from 10 mol % to 50 mol % methanol and/or methanol derivative, e.g., from 10 mol % to 40 mol %, or from 15 mol % to 30 mol %.

Vapor stream 120 may be purged or flared. In preferred embodiments, vapor stream 120 comprises substantially less carbon monoxide, and more preferably essentially no carbon monoxide, than derivative stream 108. In addition, a portion of vapor stream 120 may be fed to one or more recovery unit(s) 121. FIG. 1 shows recovery unit 121. A scrubbing solvent is fed via line 122. Preferably the solvent that is chilled to less than 25° C. may be fed to recovery unit 121 to scrub vapor stream 120 of low boiling point components, such as methyl iodide, which are removed via line 123 and are preferably returned to the reaction zone 101. Exemplary scrubbing solvents include methanol, methyl acetate, dimethyl ether, acetic acid and mixtures thereof. The overheads of recovery unit 121 may exit as purge gas 124.

FIGS. 2a and 2b show reaction/separation process 200, which comprises exemplary reaction zone 201 and exemplary separation zone 202. Reaction zone 201 comprises first reactor 130, flasher 131 and a reactor recovery unit 132. In FIGS. 1, 2a and 2b, like numbers indicate similar items.

In one embodiment, carbon monoxide, e.g., in the gaseous state, is continuously introduced into first reactor 230, desirably below an optional agitator, which may be used to stir the contents. Methanol is fed to first reactor 230 via methanol feed 204. The temperature of first reactor 230 may be controlled, as indicated above. Carbon monoxide feed 205 is introduced at a rate sufficient to maintain the desired total reactor pressure.

The gaseous feed is preferably thoroughly dispersed through the reaction medium by the stirring means. Gaseous purge is desirably vented via off-gas line 232 from first reactor 230. Off-gas vent 232 prevents buildup of gaseous by-products, such as methane, carbon dioxide, and hydrogen, and to maintain a set carbon monoxide partial pressure at a given total reactor pressure. Off-gas vent 232 is not a derivative stream, as discussed above. As shown in FIGS. 2a and 2b, a reactor recovery unit 233 may be utilized to remove low boiling point components from the vented gas in line 232. The gaseous purge streams from first reactor 230 may be combined or scrubbed separately and are typically scrubbed with either acetic acid, methanol, or mixtures of acetic acid and methanol to prevent loss of low boiling components such as methyl iodide from the process. If methanol is used as the vent scrub liquid solvent, the enriched methanol (containing methyl iodide) from reactor recovery unit 233 is typically returned to the process, e.g., via line 234, although it can also be returned into any of the streams that recycle back to the reactor such as the flasher residue or light ends or dehydration column overhead streams. If acetic acid is used as the vent scrub liquid solvent, the enriched acetic acid (containing methyl iodide) from the scrubber is typically stripped of absorbed light ends and the resulting lean acetic acid is recycled back to the scrubber (not shown). The light end components stripped from the enriched acetic acid scrubbing solvent may be returned to the main process directly, e.g., via line 234, or indirectly in several different locations including the first reactor 230, flasher 231, e.g., via line 235, or a suitable area in the separation zone 202. In one embodiment, the stream exiting the top of reactor recovery unit 233 is exited via line 239 to further processing, which may entail, for example, further separation or scrubbing. Preferably, the contents of line 236, which may contain, inter alia, (residual) carbon monoxide and methanol, may be further reacted, preferably in secondary reaction zone 203, to produce additional acetic acid. Optionally, the gaseous purge streams may be vented through the flasher base liquid or lower part of the light ends column to enhance rhodium stability and/or they may be combined with other gaseous process vents (such as the purification column overhead receiver vents) prior to scrubbing.

The crude acetic acid product is drawn off from first reactor 230 at a rate sufficient to maintain a constant level therein and is provided to flasher 231 via stream 236. In flasher 231, the crude product is separated in a flash separation step to obtain a volatile ("vapor") overhead stream 237 comprising acetic acid and a less volatile stream 238 comprising a catalyst-containing solution. The catalyst-containing solution comprises acetic acid containing the rhodium and the iodide salt along with lesser quantities of methyl acetate, methyl iodide, and water. Less volatile stream 238 preferably is recycled to first reactor 230. Beneficially, at least a portion of this stream may be directed to a second reactor in which the catalyst is used to form additional acetic acid. Streams 238' and 238" show a portion of steam 238 being directed to second reactor 211. Although FIG. 2a shows both of these streams being directed to second reactor 211, in some embodiments, only one of the streams is directed to the reactor. In other embodiments, streams 238' and 238" are not present, e.g., all of stream 238 is recycled to first reactor 230. By employing a homogeneous reactor as the secondary reactor, the recycle of catalyst in these lines is facilitated. This recycle advantageously provides for improved process efficiencies. In other embodiments, fresh catalyst may be provided to second reactor 211. The fresh catalyst, e.g., rhodium, may be the only catalyst supplied to second reactor 211 or, in the alternative, may be combined with rhodium supplied via catalyst recycle streams. Vapor overhead stream 237 also comprises methyl iodide, methyl acetate, water, PRCs. The dissolved and/or entrained gases that exit first reactor 230 and enter flasher 231 comprise a portion of the carbon monoxide and may also contain gaseous by-products such as methane, hydrogen, and carbon dioxide. The dissolved gases exit the flasher 231 as part of overhead stream 237. In some embodiments, the low-boiling overhead vapor stream 237 may be fed to the secondary reaction zone 203, e.g., to second reactor 111 (not shown).

Overhead stream 237 from flasher 231 is directed to separation zone 202. Separation zone 202 comprises light ends column 240, decanter 241, and drying column 242. Additionally, separation zone 202 may also comprise one or more columns for removing permanganate reducing compounds ("PRCs"), guard beds, heavy ends columns, extractors, etc.

In light ends column 240, stream 237 yields a low-boiling overhead vapor stream 243, a purified acetic acid product that preferably is removed via a side stream 244, and a high boiling residue stream 245. Acetic acid removed via side stream 244 preferably is subjected to further purification, such as in drying column 242 for selective separation of acetic acid from water and/or an optional heavy ends column (not shown), as described in U.S. Pat. No. 6,627,770, the entirety of which is hereby incorporated by reference. Preferably, side stream 244 and residue stream 245 comprise substantially no carbon monoxide or no detectable amounts of carbon monoxide. The residue exiting light ends column 240 may comprise catalyst. In some embodiments, at least a portion of the residue stream in line 245 may be directed to second reactor 211.

The low-boiling overhead vapor in line 243 may comprise dissolved and/or entrained carbon monoxide; methyl iodide; methyl acetate; hydrogen; water; PRCs; acetic acid; inerts such as nitrogen, argon, and helium; and other dissolved gases. In terms of upper limits, the low-boiling overhead vapor in line 243 may comprise less than 25 mol % carbon monoxide, e.g., less than 15 mol %; less than 10 mol %, or less than 5 mol %; and/or may have a carbon monoxide partial pressure less than 25% of the total pressure of the low-boiling overhead vapor, e.g., less than 15%, less than 10%, or less than 5%. Preferably, the amount of dissolved and/or entrained carbon monoxide in line 243 preferably is less than the amount of carbon monoxide in feed stream 205, e.g., at least 5% less, at least 10% less, at least 25% less, or at least 50% less. In terms of ranges, the amount of carbon monoxide in line 243 may range from 0.1 mol % to 25 mol %, e.g., from 0.5 mol % to 15 mol %, or from 1 mol % to 10 mol %; or the carbon monoxide partial pressure may range from 0.1% to 25% of the total pressure of low-boiling overhead vapor, e.g., from 0.5% to 15% of from 1% to 10%. Preferably, the low-boiling overhead vapor in line 243 comprises at least 0.1 mol % carbon monoxide, e.g., at least 0.5 mol %, or at least 1 mol %; and/or has a carbon monoxide partial pressure of at least 0.1% of the total pressure of the low-boiling overhead vapor, e.g., at least 0.5% or at least 1%. Also, the low-boiling overhead vapor in stream 243 may comprise at least 0.1 mol % methyl iodide, e.g., at least 1 mol %, or at least 5 mol %. In terms of ranges, stream 243 may comprise from 0.1 mol % to 30 mol % methyl iodide, e.g., from 1 mol % to 25 mol %, or from 5 mol % to 20 mol %. In some embodiments, the derivative stream of the crude acetic acid product in line 243 may be fed to the secondary reaction zone 203.

It has been disclosed in U.S. Pat. Nos. 6,143,930 and 6,339,171 that there is generally a higher concentration of PRCs, and in particular acetaldehyde, in the low-boiling overhead vapor stream 243 exiting the light ends column 240 than in the high-boiling residue stream 245. In some embodiment, low-boiling overhead vapor stream 240, containing PRCs, optionally may be subjected to additional processing in a PRC removal system ("PRS") (not shown) to reduce and/or remove the amount of PRCs present (or a portion thereof). PRCs are formed during the carbonylation of methanol in the presence of a Group VIII metal carbonylation catalyst. PRCs, may include, for example, compounds such as acetaldehyde, acetone, methyl ethyl ketone, butyraldehyde, crotonaldehyde, 2-ethyl crotonaldehyde, 2-ethyl butyraldehyde and the like, and the aldol condensation products thereof.

As shown, low-boiling overhead vapor stream 243, is preferably condensed and directed to an overhead phase separation unit, as shown by overhead receiver decanter 241.

Conditions are desirably maintained in the process such that low-boiling overhead vapor stream 243, once in decanter 241, will separate into a light phase and a heavy phase. Generally, low-boiling overhead vapor stream 243 is cooled to a temperature sufficient to condense and separate the condensable methyl iodide, methyl acetate, acetaldehyde and other carbonyl components, and water into two phases. A gaseous portion of stream 243 may include carbon monoxide, and other noncondensable gases such as carbon dioxide, hydrogen, and the like and is vented from the decanter 241 via line 246. Line 246 preferably has a partial pressure of carbon monoxide of less than 95% of the total pressure of line 246, e.g., less than 80%; less than 75%; less than 60%; less than 50%; or less than 40%. As used herein, all partial pressures are based upon the total pressure of all non-condensable components in the specified stream or vessel. Additionally or alternatively, line 246 may comprise less than 95 mol % carbon monoxide, e.g., less than 80 mol %; less than 75 mol %; less than 60 mol %; less than 50 mol %; or less than 40 mol %. Line 246 preferably has a carbon monoxide partial pressure and/or a weight percentage that is lower than carbon monoxide feed stream 205, which feeds first reactor 230, e.g., 5% lower; 10% lower; 25% lower or 50% lower. In terms of ranges, the amount of carbon monoxide in line 246 optionally ranges from 50 mol % to 95 mol %, e.g., from 60 mol % to 80 mol %, or from 65 mol % to 75 mol %. Optionally, line 246 has a carbon monoxide partial pressure of from 50% to 95% of the total pressure of line 246, e.g., from 60% to 80% or from 65% to 75%. Line 246 preferably has a mole percentage of methyl acetate that optionally ranges from 10 mol % to 60 mol %, e.g., from 15 mol % to 50 mol %, or from 25 mol % to 45 mol %; and/or a methyl acetate partial pressure of from 10% to 60% of the total pressure of line 246, e.g., from 15% to 50% or from 25% to 45%. This derivative stream in line 246 comprising carbon monoxide may be directed to secondary reaction zone 203, for reaction with methanol to form additional acetic acid, as discussed above in FIG. 1.

The condensed light phase 247 in decanter 241 preferably comprises water, acetic acid, and PRCs, as well as quantities of methyl iodide and methyl acetate. The condensed heavy phase 248 in decanter 241 will generally comprise methyl iodide, methyl acetate, and PRCs. The condensed heavy liquid phase 248 in the decanter 241 can be conveniently recirculated, either directly or indirectly, to first reactor 230 and/or to second reactor 211. For example, a portion of this condensed heavy liquid phase 248 can be recirculated to first reactor 230 and/or second reactor 211, with a slip stream (not shown), generally a small amount, e.g., from 5 to 40 vol. %, or from 5 to 20 vol. %, of the heavy liquid phase being directed to a PRS. This slip stream of the heavy liquid phase 248 may be treated individually or may be combined with the condensed light liquid phase 247 for further distillation and extraction of carbonyl impurities in accordance with one embodiment of the present invention.

As shown in FIGS. 2a and 2b, the light phase exits decanter 241 via stream 247. A first portion, e.g., aliquot portion, of light phase stream 247 may be recycled to the top of light ends column 240 as a reflux stream. A second portion, e.g., aliquot portion, of light phase stream 247 may be directed to the optional PRS (not shown), e.g., as shown by stream 249. A third portion, e.g., aliquot portion, of light phase stream 247 optionally may be recycled to first reactor 230, e.g., as shown by optional recycle stream 250, when additional water is desired or needed in reactor 230 or to second reactor 211. In preferred aspects the water level in the reactor is maintained at a desired level without recycling stream 250 to reactor 230 since recycling stream 250 to the reactor 230 undesirably will result in the recycle of acetic acid and unnecessarily increasing the load on reactor 230.

Light ends column 240 also preferably forms a residuum or bottoms stream 245, which comprises primarily acetic acid and water. Since light ends bottoms stream 245 typically will comprise some residual catalyst, it may be beneficial to recycle all or a portion of the light ends bottoms stream 245 to first reactor 230 (and/or second reactor 211). As shown, at least a portion of stream 245 may be directed to second reactor 211, via stream 245'. In one embodiment, stream 245' may be combined with stream 238' and/or 238" before being fed to second reactor 211. Stream 245' has the same advantages as streams 238' and 238". Preferably, the light ends bottoms stream 245 may be combined with catalyst phase 238 from flasher 231 and returned together to first reactor 230.

As indicated above, in addition to the overhead phase, the light ends column 240 also forms an acetic acid side stream 244, which preferably comprises primarily acetic acid and water. Optionally, a portion of side stream 244 may be recirculated to the light ends column, preferably to a point below where side stream 244 was removed from light ends column, as described in US Pub. No. 2008/0287706, the entirety of which is hereby incorporated by reference.

Since side stream 244 contains water in addition to acetic acid, side stream 244 from the light ends column 240 preferably is directed to a drying column 242, in which the acetic acid and water are separated from one another. As shown, drying column 242, separates acetic acid side stream 244 into an overhead stream 251 comprised primarily of water and a bottoms stream 252 comprised primarily of purified, dried acetic acid. Overhead stream 251 preferably is cooled and condensed in a phase separation unit, e.g., decanter 253, to form a light phase 254 and a heavy phase 255. As shown, a portion of the light phase 254 is refluxed, as shown by stream 256 and the remainder of the light phase is returned to first reactor 230, as shown by stream 257. The heavy phase, which typically is an emulsion comprising water and methyl iodide, preferably is returned in its entirety to the first reactor 230, as shown by stream 255, optionally after being combined with stream 257, although a portion may also be further processed (not shown). In other embodiments, at least a portion of the heavy phase may be directed to second reactor 211.

The drying column bottoms stream 252 preferably comprises or consists essentially of acetic acid. In preferred embodiments, the drying column bottoms stream comprises acetic acid in an amount greater than 90 mol %, e.g., greater than 95 mol % or greater than 98 mol %. Optionally, the drying column bottoms stream 252 may be further processed, in a heavy ends column (not shown) or iodide guard bed (not shown), prior to being stored or transported for commercial use.

Returning to vent gas stream 246 from the overhead decanter 241 of the light ends column 240. In a preferred embodiment, vent gas stream 246, which comprises an amount of residual carbon monoxide, may be directed to secondary reaction zone 203. In FIG. 2a, the vent gas stream 246 is initially processed in a recovery unit 260 to remove any low boiling point compounds, such as methyl iodide.

A scrubbing solvent, preferably chilled to less than 25° C., may be fed via line 261 to recovery unit 260 to scrub vapor stream 246 of low boiling point components, such as methyl iodide, which are removed via line 262 and are preferably returned to the reaction zone 201. Scrubbing solvents include methanol, methyl acetate, dimethyl ether, acetic acid and mixtures thereof. The overheads of recovery unit 260 may exit as purge gas 263. In one optional embodiment, a portion of the vent gas stream 246 may by-pass the recovery unit 260 in line 264 and be combined with purge gas 263.

Purge gas 263 exiting the top of recovery unit 260 comprises carbon monoxide, methyl acetate, and optionally methyl iodide. In preferred embodiments, purge gas 263 passes through compressor 265 to form compressed derivative stream 266. In preferred embodiments, the total pressure of the vapor in high pressure derivative stream 266 is from 0.1 MPa to 10 MPa, e.g., 0.5 MPa to 5 MPa or 0.5 MPa to 2 MPa. By employing a homogeneous reactor, the compression of purge gas 263, beneficially, may be reduced or minimized. In one embodiment, purge gas 263 comprises substantially no methyl iodide, which has been removed by the recovery unit 260. The compressed derivative stream 266 is fed to the secondary reaction zone 203 in FIG. 2a. Secondary reaction zone 203 comprises secondary reactor 211 as described above in FIG. 1. Secondary crude product stream 216 exits second reactor 211 and comprises acetic acid. Secondary crude product stream may also comprise methyl iodide, catalyst, methyl acetate, water, and mixtures thereof. In some embodiments, secondary crude product stream 216 may be directed to reaction zone 201. Preferably, at least a portion of secondary crude product stream 216 is fed to flasher 231 and/or to light ends column 240. Derivative stream 210 from the heavy phase stream 248 may be directed and fed to second reactor 211 with the liquid stream 219.

In FIG. 2b, vent gas stream 246 is fed to secondary reaction zone 203. In one embodiment, vent gas stream 246 from overhead decanter 241 may pass through compressor 267 to form a compressed derivative stream 268, which is fed directly to secondary reactor 211 as shown. In preferred embodiments, the total pressure of the vapor in compressed derivative stream 268 is from 0.1 MPa to 10 MPa, e.g., 0.5 MPa to 5 MPa or 0.5 MPa to 2 MPa. Compressed derivative stream 268 in FIG. 2b may comprise a higher amount of methyl iodide relative to the high pressure derivative stream 266 taught in FIG. 2a. In alternative embodiments, vent gas stream 246 may be fed as the derivative stream to second reactor 211, without being compressed or processed in a recovery unit. In the embodiments of FIG. 2b, the need for recovery unit 260 can be reduced or eliminated.

Of course, the separation systems of FIGS. 1, 2a, and 2b are merely examples of separation schemes that may be utilized in the present invention. Other combinations of separation units may just as easily be utilized. Preferable separation systems are those wherein at least a portion of residual carbon monoxide is separated and/or recovered from the crude acetic acid product.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic acid, comprising
reacting a first reaction mixture comprising carbon monoxide and at least one of methanol, methyl acetate, dimethyl ether, methyl formate, and dimethyl carbamate in a first reactor under conditions effective to produce a crude acetic acid product;
separating, in a separation zone, the crude acetic acid product into at least one derivative stream comprising residual carbon monoxide;
reacting a second reaction mixture comprising at least a portion of the residual carbon monoxide in the at least one derivative stream and at least one of methanol, methyl acetate, dimethyl ether, methyl formate, and dimethyl carbamate in a second reactor to produce additional acetic acid,
wherein the second reactor is a homogeneous reactor and a reactor carbon monoxide partial pressure is less than 1.05 MPa.

2. The process of claim 1, wherein the second reactor carbon monoxide partial pressure ranges from 0.005 MPa to 1.05 MPa.

3. The process of claim 1, further comprising the step of:
compressing the at least one derivative stream to form a compressed derivative stream, wherein the compressed derivative stream has a feed carbon monoxide partial pressure of at least 0.03 MPa.

4. The process of claim 1, further comprising the step of:
compressing the at least one derivative stream to form a compressed derivative stream, wherein the compressed derivative stream has a feed carbon monoxide partial pressure ranging from 0.03 MPa to 1.75 MPa.

5. The process of claim 1, wherein the second reactor contains a liquid catalyst.

6. The process of claim 5, wherein, in the second reactor, the at least one of methanol, methyl acetate, dimethyl ether, methyl formate, and dimethyl carbamate, and the metal catalyst are liquids.

7. The process of claim 1, wherein the first reaction mixture further comprises a first amount of rhodium and the second reaction mixture further comprises a second amount of rhodium.

8. The process of claim 7, wherein the first amount of rhodium is less than the second amount of rhodium.

9. The process of claim 1, wherein the first reactor contains catalyst and wherein the crude acetic acid product comprises catalyst.

10. The process of claim 9, further comprising the step of:
separating the crude acetic acid product to form a catalyst recycle stream comprising catalyst.

11. The process of claim 10, further comprising the step of:
directing at least a portion of the catalyst recycle stream to the second reactor.

12. The process of claim 1, wherein an overall conversion of carbon monoxide is greater than 90%.

13. The process of claim 1, wherein the second reactor yields a product stream comprising less than 40 mol % carbon monoxide.

14. The process of claim 1, wherein a pressure in the second reactor is less than the pressure in the first reactor.

15. The process of claim 1, wherein the at least one derivative stream comprising residual carbon monoxide, comprises:

from 10 mol % to 95 mol % carbon monoxide; and from 0.1 mol % to 40 mol % at least one of methanol, methyl acetate, dimethyl ether, methyl formate, and dimethyl carbamate.

16. The process of claim 1, wherein the reaction temperature in the second reactor ranges from 100° C. to 250° C.

17. The process of claim 1, wherein the at least one of methanol, methyl acetate, dimethyl ether, methyl formate, and dimethyl carbamate, in the second reactor is provided by a supplemental feed stream or another of the derivative streams.

18. The process of claim 1, wherein the at least one of methanol, methyl acetate, dimethyl ether, methyl formate, and dimethyl carbamate is methyl acetate.

19. The process of claim 1, wherein the at least one of methanol, methyl acetate, dimethyl ether, methyl formate, and dimethyl carbamate is dimethyl ether.

20. The process of claim 1, wherein the first reactor comprises a catalyst; and wherein the separating comprises:

flashing the crude acetic acid product into a first vapor stream comprising acetic acid, residual carbon monoxide and catalyst and a first liquid residue stream comprising catalyst; and separating the flashed vapor stream into a second vapor stream comprising carbon monoxide, a purified acetic acid product, and a second liquid residue stream comprising catalyst.

21. The process of claim 20, wherein at least a portion of the second liquid residue stream is directed to the second reactor.

22. The process of claim 20, wherein the separating comprises:

decanting the second vapor stream to form a third vapor stream comprising residual carbon monoxide and a third liquid residue stream comprising methyl iodide, methyl acetate, acetaldehyde; and compressing the third vapor stream to form a compressed derivative stream.

* * * * *